US010813903B2

(12) United States Patent
Rowe et al.

(10) Patent No.: US 10,813,903 B2
(45) Date of Patent: *Oct. 27, 2020

(54) COMPOSITIONS COMPRISING 15-HEPE AND METHODS OF USING THE SAME (71) Applicant: Afimmune Limited, Dublin (IE)

(72) Inventors: Jonathan Rowe, Waterford, CT (US); Kevin Duffy, Dublin (IE); John Climax, Dublin (IE)

(73) Assignee: Afimmune Limited (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/527,841

(22) Filed: Jul. 31, 2019

(65) Prior Publication Data

US 2020/0069626 A1 Mar. 5, 2020

Related U.S. Application Data (63) Continuation of application No. 14/695,865, filed on Apr. 24, 2015, now abandoned, which is a continuation of application No. PCT/EP2014/051455, filed on Jan. 24, 2014.

(30) Foreign Application Priority Data

Jan. 30, 2013 (GB) .................................. 1301626.6

(51) Int. Cl.
*A61K 31/202* (2006.01)
*A61K 9/48* (2006.01)
*A61K 9/00* (2006.01)
*A61P 1/16* (2006.01)
*A61K 31/557* (2006.01)

(52) U.S. Cl.
CPC .......... *A61K 31/202* (2013.01); *A61K 9/0053* (2013.01); *A61K 9/48* (2013.01); *A61K 31/557* (2013.01); *A61P 1/16* (2018.01)

(58) Field of Classification Search
CPC ...... A61K 31/202; A61K 31/557; A61K 9/48; A61P 1/16
See application file for complete search history.

(56) References Cited

U.S. PATENT DOCUMENTS

| 7,579,362 | B2 | 8/2009 | Feuerbach et al. |
| 8,293,790 | B2 | 10/2012 | Manku et al. |
| 9,050,308 | B2 | 6/2015 | Maines et al. |
| 9,855,238 | B2 | 1/2018 | Coughlan et al. |
| 10,231,945 | B2 | 3/2019 | Coughlan et al. |
| 10,363,235 | B2 * | 7/2019 | Rowe .................. A61K 31/557 |
| 2002/0055538 | A1 | 5/2002 | Serhan et al. |
| 2004/0043013 | A1 | 3/2004 | McCleary |
| 2005/0239889 | A1 | 10/2005 | Gosselin |
| 2005/0282781 | A1 | 12/2005 | Ghosal |
| 2006/0009522 | A1 | 1/2006 | Dana et al. |
| 2007/0105954 | A1 | 5/2007 | Puri |
| 2010/0233724 | A1 | 9/2010 | Watkins et al. |
| 2011/0059885 | A1 | 3/2011 | Lea et al. |
| 2011/0105510 | A1 | 5/2011 | Ishikawa |
| 2012/0142773 | A1 | 6/2012 | Kelliher et al. |
| 2012/0213824 | A1 | 8/2012 | Kelliher et al. |
| 2012/0232147 | A1 | 9/2012 | Manku et al. |
| 2012/0264705 | A1 | 10/2012 | Manku et al. |
| 2012/0264824 | A1 | 10/2012 | Mizuguchi et al. |
| 2013/0101533 | A1 | 4/2013 | Manku et al. |
| 2013/0102575 | A1 | 4/2013 | Manku et al. |
| 2013/0267598 | A1 | 10/2013 | Manku et al. |
| 2013/0274338 | A1 | 10/2013 | Manku et al. |
| 2013/0310422 | A1 | 11/2013 | Brown et al. |
| 2014/0079631 | A1 | 3/2014 | Serhan et al. |
| 2015/0224076 | A1 * | 8/2015 | Rowe .................. A61K 9/48 514/560 |

FOREIGN PATENT DOCUMENTS

| EP | 2762143 | 8/2014 |
| JP | H07126160 | 5/1995 |
| JP | H09505562 | 6/1997 |
| JP | 2000191525 | 7/2000 |
| JP | A2003525880 | 9/2003 |
| JP | 2005179211 | 7/2005 |
| JP | 2013517304 | 5/2013 |
| WO | WO 02/096408 | 12/2002 |
| WO | WO 2010/125340 | 11/2010 |
| WO | WO 2013/057284 | 4/2013 |
| WO | WO 2013/057287 | 4/2013 |
| WO | WO 2013/082265 | 6/2013 |
| WO | WO 2013/112876 | 8/2013 |
| WO | WO 2013/124479 | 8/2013 |
| WO | WO 2013/170006 | 11/2013 |
| WO | WO-2013170006 A2 * | 11/2013 |
| WO | WO 2014/118097 | 8/2014 |
| WO | WO 2016/090030 | 6/2016 |

OTHER PUBLICATIONS

Martinez-Clemente et al. (2010) Hepatology; 51: 817-827. (Provided from U.S. Appl. No. 14/695,865).*
Miller et al. (1989) Lipids 24, 998-1003 (Provided from U.S. Appl. No. 14/695,865).*
Kajikawa et al. Dig Dis Sci; (2010) 56(4): 1065-74. (Provided from U.S. Appl. No. 14/695,865).*
CDER (Guidance for Industry: Estimating the Maximum Safe Starting Dose in Initial Clinical Trials for Therapeutics in Adult Healthy Volunteers; 2005. (Provided from U.S. Appl. No. 14/695,865).*
"Blood sample volumes," National Centre for the Replacement Refinement & Reduction of Animals in Research (adapted Wolfensohn & Lloyd, 2003, Handbook of Laboratory Animal Management and Welfare, 3rd Edition) (publication date: Nov. 28, 2003) (https://www.nc3rs.org.uk/blood-sample-volumes; accessed Mar. 27, 2019).
AASLD Abstracts. Hepatology, 598A-702A (publication date: Oct. 2005).
Argo et al., "Effects of N-3 Fish Oil on Metabolic and Histological Parameters in NASH: A Double-Blind, Randomized, Placebo-Controlled Trial," Journal of Hepatology, (publication date: Jan. 2015, epublication date: Sep. 6, 2014).

(Continued)

*Primary Examiner* — Yong L Chu
(74) *Attorney, Agent, or Firm* — Perkins Coie LLP (57) ABSTRACT

The present invention relates to the compositions, formulations and methods of treating fatty liver disorders, such as non-alcoholic fatty liver disease (NAFLD) and non-alcoholic steatohepatitis (NASH) and their sequelae by administration of 15-OHEPA.

24 Claims, 3 Drawing Sheets

(56) References Cited

OTHER PUBLICATIONS

Astarita, et al., "Targeted lipidomic strategies for oxygenated metabolites of polyunsaturated fatty acids," Biochimica et Biophysica Acta 1851, pp. 456-468 (publication date: Apr. 2015, epublication date: Dec. 5, 2014).
Baskin-Bey, Edwina S. et al., "Constitutive androstane receptor agonist, TCPOBOP, attenuates steatohepatitis in the methionine choline-deficient diet-fed mouse," Online Submissions: wjg.wjgnet.com; World J Gastroenterol, 13(42): pp. 5635-5641 (publication date: Nov. 14, 2007).
Brooks et al., "The fatty acid oxidation product 15-A3t-isoprostane is a potent inhibitor of NFκB transcription and macrophage transformation," Journal of Neurochemistry 119:604-616 (publication date: Nov. 2011, epublication date: Sep. 23, 2011).
Center for Drug Evaluation and Research, "Guidance for Industry Estimating the Maximum Safe Starting Dose in Initial Clinical Trials for Therapeutics in Adult Healthy Volunteers," Pharmacology and Toxicology (publication date: Jul. 2005).
Chalasani, Naga et al., "The Diagnosis and Management of Non-Alcoholic Fatty Liver Disease: Practice Guideline by the American Association for the Study of Liver Diseases, American College of Gastroenterology, and the American Gastroenterological Association," Hepatology, vol. 55, No. 6, pp. 2005-2023 (publication date: Jun. 2012).
Contrera et al., "Estimating the safe starting dose in phase I clinical trials and no observed effect level based on QSAR modeling of the human maximum recommended daily dose," Requl Toxicol Pharmacol (publication date: Dec. 2004, epublication date: Oct. 2, 2004).
Das, "A defect in the activities of Δ6 and Δ5 desaturases and pro-resolution bioactive lipids in the pathobiology of non-alcoholic fatty liver disease," World Journal of Diabetes 2(11):176-188 (publication date: Nov. 15, 2011).
Depner et al., "Docosahexaenoic Acid Attenuates Hepatic Inflammation, Oxidative Stress, and Fibrosis without Decreasing Hepatosteatosis in a Ldlr2/2 Mouse Model of Western Diet-Induced Nonalcoholic Steatohepatitis^(1-3)," The Journal of Nutrition, pp. 315-323 (publication date: Mar. 2013, epublication date: Jan. 9, 2013).
Di Minno et al., "Omega-3 fatty acids for the treatment of non-alcoholic fatty liver disease," World Journal of Gastroenterology 18(41): pp. 5839-5847 (epublication date: Nov. 7, 2012).
Ding et al., "Regulation of Adipokines by Polyunsaturated Fatty Acids in a Rat Model of Non-alcoholic Steatohepatitis," Arch Iran Med, 17(8): pp. 563-568. (publication date: Aug. 2014).
Flachs et al., "Synergistic induction of lipid catabolism and anti-inflammatory lipids in white fat of dietary obese mice in response to calorie restriction and n-3 fatty acids," Diabetologia, 54(10):2626-2638 (publication date: Oct. 2011, epublication date: Jul. 21, 2011).
Granlund et al., "Effects of structural changes of fatty acids on lipid accumulation in adipocytes and primary hepatocytes," Biochimica et Biophysica Acta 1687(1-3):23-30 (publication date: Feb. 21, 2005, epublication date: Nov. 28, 2004).
International Search Report and Written Opinion dated Feb. 3, 2016 for International Application No. PCT/US2015/63488.
International Search Report and Written Opinion dated Jun. 6, 2016 for International Application No. PCT/IB2016/000202.
International Search Report and Written Opinion dated Mar. 27, 2014 for PCT/EP14/51455.
Ishii et al., "Eicosapentaenoic acid ameliorates steatohepatitis and hepatocellular carcinoma in hepatocyte-specific Pten-deficient mice," Journal of Hepatology, 50:562-571 (publication date: Mar. 1, 2009, epublication date: Dec. 27, 2008).
Ivy et al., "Approaches to Phase 1 Clinical Trail Design Focused on Safety, Efficiency, and Selected Patient Populations: A Report from the Clinical Trail Design Task Force of the National Cancer Institute Investigational Drug Steering Committee," Clin Cancer Res (publication date: Mar. 15, 2010, epublication date: Mar. 9, 2010).

Kajikawa et al., "Eicosapentaenoic acid attenuates progression of hepatic fibrosis with inhibition of reactive oxygen species production in rats fed methionine- and choline-deficient diet," Dig Dis Sci 56(4):1065-74 (publication date: Apr. 2011, epublication date: Sep. 17, 2010).
Kendall et al., "Distribution of Bioactive Lipid Mediators in Human Skin," The Journ. of Investigative Dermatology. 00:1-11 (publication date: Jun. 2015, epublication date: Mar. 12, 2015).
Kucera, Otto et al., "Experimental models of non-alcoholic fatty liver disease in rats," World J Gastroenterol, 20(26): pp. 8364-8376 (epublication date: Jul. 14, 2014).
Lam et al., "Transformation of 15-Hydroperoxyeicosapentaenoic acid into mono- and dihydroeicosapentaenoic acids by human platelets," Drugs Affecting Leukotrienes and Other Eicosanoid Pathways 95:167-180 (1985).
Lam et al., "Treatment options for nonalcoholic fatty liver disease," Therapeutic Advances in Gastroenterology 3(2):121-137 (publication date: Mar. 2010).
Larsson et al., "Dietary long-chain n-3 fatty acids for the prevention of cancer: a review of potential mechanisms," The American Journal of Clinical Nutrition 79(6):935-45 (publication date: Jun. 2004).
Mahady, Suzanne et al., "Management of Nonalcoholic Steatohepatitis, An Evidence-Based Approach," Clin Liver Dis 16(3):631-645 (publication date: Aug. 2012, epublication date: Jun. 20, 2012).
Malholtra et al., "Management of non-alcoholic fatty liver disease in 2015," World Journal of Hepatology, 7(30):2962-2967 (publication date: Dec. 28, 2015).
Martinez-Clemente et al., "5-Lipoxygenase Deficiency Reduces Hepatic Inflammation and Tumor Necrosis Factor α-Induced Hepatocyte Damage in Hyperlipidemia-Prone ApoE-Null Mice," Hepatology 51:817-27 (publication date: Mar. 2010).
Masterton et al., "Review article: omega-3 fatty acids—a promising novel therapy for non-alcoholic fatty liver disease," Alimentary Pharmacology & Therapeutics, 31(7):679-692 (publication date: Apr. 30, 2010, epublication date: Mar. 1, 2010).
Miller et al., "Dietary Supplementation with Ethyl Ester Concentrates of Fish Oil (N-3) and Borage Oil (N-6) Polyunsaturated Fatty Acids Induces Epidermal Generation of Local Putative Anti-Inflammatory Metabolites," The Journ. Of Invest. Dermatol., vol. 96, No. 1, pp. 98-103 (publication date: Jan. 1991).
Miller et al., "Guinea Pig Epidermis Generates Putative Anti-Inflammatory Metabolites from Fish Oil Polyunsaturated Acids," Lipids 24(12):998-1003 (publication date: Dec. 1989).
Nguyen et al., "Mechanisms for anti-inflammatory effects of 1-[15(S)-hydroxyeicosapentaenoyl] lysophosphatidylcholine, administered intraperitoneally, in zymosan A-induced peritonitis," British Journal of Pharmacology 162(5):1119-1135 (publication date: Mar. 2011, epublication date: Nov. 22, 2010).
Parker et al., "Omega-3 supplementation and non-alcoholic fatty liver disease: a systematic review and meta-analysis," J Hepatol. 56(4):944-51 (publication date: Apr. 2012, epublication date: Oct. 21, 2011).
Pereira et al., "Identification of two novel microalgae enzymes involved in the conversion of the w3-fatty acid, eicosapentaenoic acid, into docosahexaenoic acid," Biochem J. 384:357-366 (publication date: Dec. 1, 2004, epublication date: Aug. 13, 2004).
Rusu E. et al., "Medical nutrition therapy in non-alcoholic fatty liver disease—a review of literature," Journal of Medicine and Life, vol. 8, Issue 3, pp. 258-262 (publication date: Jul.-Sep. 2015).
Sanyal, Arun J. et al., "No Significant Effects of Ethyl-Eicosapentanoic Acid on Histologic Features of Nonalcoholic Steatohepatitis in a Phase 2 Trial," Gastroenterology, vol. 147, No. 2, pp. 377-384 (publication date: Aug. 2014, epublication date: May 9, 2014).
Serhan et al., "Novel Pro-resolving Aspirin-Triggered DHA Pathway," Chem. Biol. 18(8):976-987 (publication date: Aug. 2011).
Serhan et al., "Resolvins and Protectins in Inflammation-Resolution," Chem Rev. 111(10):5922-5943 (publication date: Oct. 12, 2011, epublication date: Jul. 18, 2011).
Serhan et al., "Resolvins: A Family of Bioactive Products of Omega-3 Fatty Acid Transformation Circuits Initiated by Aspirin (56) References Cited

OTHER PUBLICATIONS

Treatment that Counter Proinflammation Signals," J. Exp. Med. 196(8)1025-1037 (publication date: Oct. 21, 2002).

Shinohara et al., "Functional metabolomics reveals novel active products in the DHA metabolome," Frontiers in Immunology, vol. 3, article 81, pp. 1-9 (publication date: Apr. 17, 2012).

Tanaka et al., "Highly-purified eicosapentaenoic acid treatment improves nonalcoholic steatohepatitis," Journal of Clinical Gastroenterology, 42(4):413-418 (publication date: Apr. 1, 2008).

Vang K, et al., "15-lipoxygenase metabolites of gamma-linolenic acid/eicosapentaenoic acid suppress growth and arachidonic acid metabolism in human prostatic adenocarcinoma cells: Possible implications of dietary fatty acids", Prostaglandins Leukot Essent Fatty Acids 72(5):363-372 (publication date: May 2005).

Osmundsen et al. "Effects of dietary treatment of rats with eicosapentaenoic acid or docosahexaenoic acid on hepatic lipid metabolism," Biochemical Journal 331(1):153-160 (publication date: Apr. 1, 1998).

Powell et al., "Metabolism of eicosapentaenoic acid by aorta: formation of a novel 13-hydroxylated prostaglandin," Biochim Biophys Acta 835(2):201-11 (publication date: Jul. 9, 1985) (Abstract only).

Proteau et al., "Divinyl ethers and hydroxy fatty acids from three species of *Laminaria* (brown algae)," Lipids 28(9):783-7 (publication date: Sep. 1993) (Abstract only).

\* cited by examiner

Figure 1. Body weight and liver weight

Figure 1.1.
Body weight

Figure 1.2.
Liver weight

*Figure 2. NAFLD Activity Score*

*Figure 2.1*

| Group | n | Steatosis | | | | Lobular inflammation | | | | Hepatocyte ballooning | | | NAS (Mean ± SD) |
|---|---|---|---|---|---|---|---|---|---|---|---|---|---|
| | | 0 | 1 | 2 | 3 | 0 | 1 | 2 | 3 | 0 | 1 | 2 | |
| Vehicle | 8 | - | 8 | - | - | - | 2 | 3 | 3 | - | - | 8 | 5.1 ± 0.8 |
| 15-OH EPA 50 mg/kg | 8 | 2 | 6 | - | - | - | 3 | 3 | 2 | - | 4 | 4 | 4.1 ± 1.2 |
| 15-OH EPA 500 mg/kg | 8 | - | 7 | 1 | - | 2 | 5 | 1 | - | - | 4 | 4 | 3.5 ± 1.2 |
| EPA 500 mg/kg | 8 | - | 7 | 1 | - | 1 | 4 | 2 | 1 | - | 3 | 5 | 4.1 ± 1.1 |
| Telmisartan | 8 | 8 | - | - | - | 3 | 4 | 1 | - | 1 | 5 | 2 | 1.9 ± 1.2 |

Figure 2.2

COMPOSITIONS COMPRISING 15-HEPE AND METHODS OF USING THE SAME

TECHNICAL FIELD

The invention pertains to the compositions, formulations and methods of treating fatty liver disorders (FLD), such as non-alcoholic fatty liver disease (NAFLD) and non-alcoholic steatohepatitis (NASH) and their sequelae by administration of a pharmaceutical composition comprising 15-hydroxy eicosapentaenoic acid (known as 15-OHEPA or 15-HEPE) in a subject in need thereof. In particular, the invention relates to a pharmaceutical composition with improved efficacy over one comprising EPA as the significant active component, rather than 15-OH EPA, for the treatment of subjects suffering from FLD and/or complications of FLD, to reduce fatty deposits in the liver to treat or prevent FLD and its associated complications.

SUMMARY

Fatty liver disorders, also known as fatty liver or fatty liver disease (FLD), relates to a condition where large vacuoles of triglyceride fat accumulate in liver cells via the process of steatosis, or abnormal retention of lipids within a cell. Despite having multiple causes, fatty liver is considered a single disease that occurs frequently in subjects with excessive alcohol intake and/or those who are obese (with or without effects of insulin resistance). The condition is also associated with other diseases that influence fat metabolism. FLD may be categorized into two separate conditions: alcoholic FLD and non-alcoholic FLD. Both conditions show micro-vesicular and macro-vesicular fatty changes at different stages of the disease. Accumulation of fat may also be accompanied by a progressive inflammation of the liver (hepatitis), called steatohepatitis. Fatty liver is also known in the art as alcoholic steatosis and non-alcoholic fatty liver disease (NAFLD), and the more severe forms as alcoholic steatohepatitis (part of alcoholic liver disease) and non-alcoholic steatohepatitis (NASH). Nonalcoholic fatty liver disease-associated cirrhosis is the most severe form of the disease and is characterized by liver inflammation that leads to scarring of the liver tissue, ultimately resulting in liver failure.

Obesity, metabolic syndrome, type 2 diabetes, and atherosclerosis are increasing at an alarming rate in the Western world. In recent years, fatty liver has emerged as an independent risk factor for these diseases. Fatty liver is the accumulation of triglycerides and other fats within hepatocytes. Fatty liver disease can range from fatty liver alone (also known as "steatosis"), to fatty liver associated with inflammation or steatohepatitis. Non-alcoholic fatty liver disease (NAFLD) and non-alcoholic steatohepatitis (NASH) are the most common causes of chronic liver disease in the adult population and represents a crucial risk factor for progression to liver failure, cirrhosis and hepatocellular carcinoma. While steatosis affects approximately 30% of the population, 80% of obese patients have NAFLD and 50% of patients undergoing bariatric surgery have steatohepatitis. NAFLD also represents the most common cause of liver disease in children. It is estimated that NAFLD affects up to 20 percent of adults and nearly 5 percent of children. Some experts estimate that about two thirds of obese adults and half of obese children may have fatty liver. In the past ten years, as the rates of obesity in have doubled in adults and tripled in children and teenagers, NAFLD and NASH are becoming more common. NASH can cause scarring and hardening of the liver, leading to cirrhosis, a very serious disease that may require a liver transplant, and eventually to hepatocellular carcinoma.

There is no single established medical treatment for fatty liver. Presently, treatment of NAFLD is limited to 1) treatment of associated metabolic disorders such as diabetes and hyperlipidemia; 2) the management of insulin resistance focusing on weight loss, exercise and/or a pharmacological approach; and 3) the use of antioxidants as hepatic protection agents. Despite the use of many different therapeutic modalities, no clear treatment is currently available to address NAFLD. Because it is clinically important to resolve NAFLD and its sequelae, new approaches aimed at preventing and reversing fat accumulation in the liver are necessary.

We have surprisingly found that 15-HEPE, a metabolite of EPA, is more potent than EPA in the treatment of FLD.

BRIEF DESCRIPTION OF THE DRAWINGS

FIGS. 1.1, 1.2, 2.1 and 2.2 present data from an in vivo efficacy study of 15-OHEPA and EPA in STAM model of non-alcoholic steatohepatitis, as discussed in the Examples herein.

Other features and advantages of the invention will be apparent from the following detailed description.

DETAILED DESCRIPTION

The present invention relates to compositions and methods for treating fatty liver disorders, including non-alcoholic fatty liver disease (NAFLD) and non-alcoholic steatohepatitis (NASH), by administration of a composition comprising 15-HEPE in a subject in need thereof.

As used herein, "15-OHEPA" is 15-Hydroxy-eicosa-5,8,11,13,17-pentaenoic acid. 15-OHEPA can be synthesized from eicosapentaenoic acid, EPA according to methods known in the art. As used herein, the term "15-OHEPA" refers to 15-OHEPA in its free acid form (e.g, 15-hydroxy-eicosa-5,8,11,13,17-pentaenoic acid) and/or a pharmaceutically acceptable ester, conjugate or salt thereof, or mixtures of any of the foregoing. A derivative of 15-OHEPA may be used instead, though this does not include any derivative compound missing the hydroxy group of 15-OHEPA. In some embodiments, the 15-OHEPA is used in the free acid form. Alternatively, pharmaceutically acceptable esters or salts of 15-OHEPA are used in the invention. In some embodiments, the 15-OHEPA is in the form of a $C_{1-4}$ alkyl ester such as methyl ester or ethyl ester form.

As used herein, "EPA" is eicosa-5,8,11,14,17-pentaenoic acid, also known as 20:5n-3, an omega-3 fatty acid. EPA is readily obtainable through commercial sources.

Accordingly, in one aspect of the present invention, a method of treating a fatty liver disorder in a subject is provided, comprising administering to the subject a therapeutically effective amount of a composition comprising 15-OHEPA.

The present invention provides 15-OHEPA, or a composition comprising 15-OHEPA, for use in the treatment of a fatty liver disorder.

The present invention provides a use of 15-OHEPA, or a composition comprising 15-OHEPA, in the manufacture of a medicament for treating a fatty liver disorder.

In another aspect, the present invention provides a pharmaceutical composition comprising a therapeutically effective amount of 15-OHEPA. The 15-OHEPA may be the sole significant active ingredient in that composition and in the methods and uses as stated herein. The 15-OHEPA may be the sole active ingredient. Alternatively, the 15-OHEPA may be combined for co-formulation or co-administration with other agents for treating FLD. If an additional active agent is to be used, the 15-OHEPA can be co-formulated as a single dosage unit or can be formulated as two to a plurality of dosage units for coordinated, combination or concomitant administration.

The invention also provides formulations of 15-OHEPA and formulations comprising 15-OHEPA and methods of using these formulations for treating fatty liver disorders, including non-alcoholic fatty liver disease (NAFLD) and non-alcoholic steatohepatitis (NASH).

15-OHEPA is a chiral molecule and may be used in the (S)- or (R)-enantiomeric form, or as a racemic mixture. Used herein, "15-OHEPA" includes all such forms, with no limitation as to stereospecifcity. In another embodiment, the 15-OHEPA comprises the (S) form: 15(S)-Hydroxy-(5Z,8Z,11Z,13E,17Z)-eicosapentaenoic acid. In some embodiments, the 15-OHEPA may be used in the form of the ethyl ester. In other embodiments the 15-OHEPA may be used as the free acid.

The present invention further provides an pharmaceutical composition for oral delivery, comprising 15-OHEPA. That composition may comprise a pharmaceutically acceptable excipient. The 15-OHEPA may be in any form as discussed herein. The 15-OHEPA may be present from about 50 mg to about 3000 mg.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Pharmaceutical Compositions

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

15-Hydroxy Eicosapentaenoic Acid

In one embodiment, compositions of the invention comprise 15-OHEPA as an active ingredient. 15-OHEPA is the abbreviation for 15-Hydroxy eicosapentaenoic acid, a metabolite of eicosapentaenoic acid (EPA) that can be synthesized via ways known in the art, such as exposure of eicospentaenoic acid to the enzyme 15-lipoxygenase. As used herein, the term "15-OHEPA" refers to 15-OHEPA in its free acid form (e.g., 15-Hydroxy eicosapentaenoic acid) and/or a pharmaceutically acceptable ester, conjugate or salt thereof, or mixtures of any of the foregoing. A derviative of 15-OHEPA may be used instead, though this does not include any derivative compound missing the hydroxy group of 15-OHEPA. The term "pharmaceutically acceptable" in the present context means that the substance in question does not produce unacceptable toxicity to the subject or interaction with other components of the composition.

In one embodiment, the 15-OHEPA is in the form of an ester (also referred to herein as E-15-OHEPA or ethyl-15-OHEPA). In another embodiment, the 15-OHEPA comprises a $C_1$-$C_5$ alkyl ester of 15-OHEPA. In another embodiment, the 15-OHEPA comprises 15-OHEPA methyl ester, 15-OHEPA propyl ester, or 15-OHEPA butyl ester. In still another embodiment, the 15-OHEPA comprises the optically active 15(S)-Hydroxy-(5Z,8Z,11Z,13E,17Z)-eicosapentaenoic acid. This isomer may be used in any of the forms discussed above.

In another embodiment, the 15-OHEPA comprises lithium 15-OHEPA, mono-, di- or triglyceride 15-OHEPA or any other ester or salt of 15-OHEPA, or the free acid form of 15-OHEPA.

In various embodiments, the invention provides pharmaceutical compositions, for example orally deliverable compositions, comprising 15-OHEPA. In one embodiment, the compositions comprise a therapeutically effective amount of 15-OHEPA. In one embodiment, the pharmaceutical composition comprises about 0.1% to about 99%, about 1% to about 95%, about 5% to about 90% by weight of 15-OHEPA.

In one embodiment, the pharmaceutical composition comprises about at least about 70%, at least about 80% or at least about 90%, by weight, of 15-OHEPA. In one embodiment, the pharmaceutical composition comprises at least about 50%, at least about 60%, at least about 70%, at least about 80% or at least about 90%, by weight of 15-OHEPA.

In another embodiment, 15-OHEPA is present in a composition of the invention in an amount of about 1 mg to about 10,000 mg, 25 mg to about 7500 mg, about 25 mg to about 5000 mg, about 50 mg to about 5000 mg, about 50 mg to about 3000 mg, about 75 mg to about 2500 mg, or about 100 mg to about 1000 mg, for example about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, or about 2500 mg.

In one embodiment, 15-OHEPA present in a composition of the invention comprises at least 90% by weight 15-OHEPA (as the term "15-OHEPA" is defined and exemplified herein). 15-OHEPA compositions can comprise even higher purity 15-OHEPA, for example at least 95% by weight 15-OHEPA or at least 97% by weight 15-OHEPA, wherein the 15-OHEPA is any form of 15-OHEPA as set forth herein. The purity of 15-OHEPA can further be defined (e.g. impurity profile) by any of the descriptions of 15-OHEPA provided herein.

Above are discussed the amounts of the 15-OHEPA in the pharmaceutical composition and their purity. The nature of the essential fatty acids and their synthesis is such that the 15-OHEPA composition may include moieties from other essential fatty acids in the essential fatty acid metabolic cascade.

In one embodiment, a composition of the invention contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of other omega-3 fatty acids including alpha linolenic acid, stearidonic acid, docosahexaenoic acid (DHA) or derivatives thereof. In other embodiments there is substantially no, or no such other omega-3 fatty acids present.

In another embodiment, 15-OHEPA represents at least about 60%, at least about 70%, at least about 80%, at least about 90%, at least about 95%, at least about 97%, at least about 98%, at least about 99%, or 100%, by weight, of all fatty acids present in a composition of the invention.

There may be present some residual eicosapentaenoic acid from the synthesis of the 15-OHEPA. There may be not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight EPA. Alternatively, there is substantially no, or no, EPA in a form which has not been modified to the hydroxyl-form.

Additional Active Agents

In one embodiment, the pharmaceutical composition further comprises one or more additional active agent(s). In one embodiment, the pharmaceutical composition comprises an amount of the additional active agent that is less than the generally recognized therapeutically effective amount for that agent. In one embodiment, the pharmaceutical composition comprises an amount of the additional active agent that is equal to or greater than the generally recognized therapeutically effective amount for that agent.

EPA itself has beneficial properties in treating FLD and it is possible to combine the 15-OHEPA with EPA in an alternative embodiment.

In one embodiment, 15-OHEPA and one or more active agent(s) are present in a composition of the invention, or are co-administered in a weight ratio of 15-OHEPA:additional agent of about 1:1000 to about 1000:1, about 1:500 to about 500:1, about 1:100 to about 100:1, about 1:50 to about 50:1, about 1:25 to about 25:1, about 1:10 to about 10:1, about 1:5 to about 5:1, about 1:4 to about 4:1 about 1:3 to about 3:1, about 1:2 to about 2:1 or about 1:1.

Dosage Forms

A composition for use in accordance with the disclosure can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In some embodiments, compositions of the invention are in the form of orally deliverable dosage forms or units. Non-limiting examples of suitable dosage forms include tablets (e.g. suspension tablets, bite suspension tablets, rapid dispersion tablets, chewable tablets, etc), caplets, capsules (e.g. a soft or a hard gelatin capsule or HPMC capsule), lozenges, sachets, cachets, troches, pellets, suspension, elixirs, syrups or any other solid dosage form reasonably adapted for oral administration. The terms "oral delivery" and "oral administration" herein include any form of delivery wherein the agent or composition is placed in the mouth of the subject under treatment, whether swallowed or not. This therefore includes buccal and sublingual administration, as well as esophagael administration.

Alternatively, compositions of the invention can also be formulated for rectal, topical, or parenteral (e.g. subcutaneous, intramuscular, intravenous and intradermal or infusion) delivery.

In discussing the amount of 15-OHEPA in a composition of the invention, this may be split over several dosage forms. There is a limit as to the size for oral administration. If a subject is to be administered 1 to 4 g 15-OHEPA a day, this may be by up to 4 capsules, each providing 1 g 15-OHEPA.

Compositions of the invention can be in the form of liquid dosage forms or dose units to be imbibed directly or they can be mixed with food or beverage prior to ingestion. Non-limiting examples of suitable liquid dosage forms include solutions, suspensions, elixirs, syrups, liquid aerosol formulations, and the like.

In another embodiment, compositions of the invention comprise one or more pharmaceutically acceptable excipients. The term "pharmaceutically acceptable excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition, and that does not produce unacceptable toxicity or interaction with other components in the composition. By way of example only, a pharmaceutical composition according to the present disclosure may comprise one or more of: antioxidants, surfactants, preservatives, flavouring agents, cosolvents, viscosity aids, suspension aids, and lipophilic phases.

In one embodiment, the pharmaceutical composition comprises one or more antioxidants such as ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, niacinamide, and the like. In one embodiment, the pharmaceutical composition comprises about 0.01 wt. % to about 2 wt. % of an antioxidant, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, about 0.5 wt. %, about 0.51 wt. %, about 0.52 wt. %, about 0.53 wt. %, about 0.54 wt. %, about 0.55 wt. %, about 0.56 wt. %, about 0.57 wt. %, about 0.58 wt. %, about 0.59 wt. %, about 0.6 wt. %, about 0.61 wt. %, about 0.62 wt. %, about 0.63 wt. %, about 0.64 wt. %, about 0.65 wt. %, about 0.66 wt. %, about 0.67 wt. %, about 0.68 wt. %, about 0.69 wt. %, about 0.7 wt. %, about 0.71 wt. %, about 0.72 wt. %, about 0.73 wt. %, about 0.74 wt. %, about 0.75 wt. %, about 0.76 wt. %, about 0.77 wt. %, about 0.78 wt. %, about 0.79 wt. %, about 0.8 wt. %, about 0.81 wt. %, about 0.82 wt. %, about 0.83 wt. %, about 0.84 wt. %, about 0.85 wt. %, about 0.86 wt. %, about 0.87 wt. %, about 0.88 wt. %, about 0.89 wt. %, about 0.9 wt. %, about 0.91 wt. %, about 0.92 wt. %, about 0.93 wt. %, about 0.94 wt. %, about 0.95 wt. %, about 0.96 wt. %, about 0.97 wt. %, about 0.98 wt. %, about 0.99 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. % of the one or more antioxidant.

Therapeutic Methods

The compositions and formulations disclosed herein may be used in the treatment of fatty liver disease. In one embodiment the fatty liver disease is non-alcoholic fatty liver disease. In another embodiment the fatty liver disease is non-alcoholic steatohepatitis. In one embodiment, the method comprises administering a pharmaceutical composition as disclosed herein to a subject once per day, twice per day, three times per day, or more than three times per day.

As used herein, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

An "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein, such as a compound of Formula (A) or Formula (I), is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician. The term "pharmaceutically acceptable" in the present context means that the substance in question does not produce unacceptable toxicity to the subject or interaction with other components of the composition.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

The purpose of this study was to examine the effects of 15-OHEPA and EPA in the STAM model of Non-alcoholic Steatohepatitis.

Protocol

Pathogen-free 15-day-pregnant C57BL/6 mice were obtained from Charles River Laboratories in Japan Inc. (Kanagawa, Japan). NASH was established in male mice by a single subcutaneous injection of streptozotocin (STZ) (Sigma, USA) after birth and feeding with a high fat diet (HFD; CLEA) Japan, Japan) ad libitum after 4 weeks of age (day 28±2). Mice were randomized into 5 groups of 8 mice at 5 weeks of age (day 35±2) the day before the start of treatment.

During the treatment period, individual body weight was measured daily as well as clinical signs of behavior and survival.

Groups:

Group 1 (Vehicle): Eight NASH mice were orally administered vehicle [olive oil] in a volume of 10 mL/kg once daily from 5 to 9 weeks of age.

Group 2 (15-OHEPA 50 mg/kg): Eight NASH mice were orally administered vehicle supplemented with 15-OHEPA at a dose of 50 mg/kg once daily from 5 to 9 weeks of age.

Group 3 (15-OHEPA 500 mg/kg): Eight NASH mice were orally administered vehicle supplemented with 15-OHEPA at a dose of 500 mg/kg once daily from 5 to 9 weeks of age.

Group 4 (EPA 500 mg/kg): Eight NASH mice were orally administered vehicle supplemented with EPA at a dose 500 mg/kg once daily from 5 to 9 weeks of age.

Group 5 (positive control): Eight NASH mice were orally administered pure water supplemented with Telmisartan at a dose of 10 mg/kg once daily from 5 to 9 weeks of age.

At 9 weeks of age, all mice were sacrificed and the following data was recorded;

Individual liver weight

Liver to body weight ratio

Histopathological analyses of liver sections were performed using HE staining (to estimate NAFLD Activity score). For HE staining, sections were cut from paraffin blocks of liver tissue prefixed in Bouin's solution and stained with Lillie-Mayer's Hematoxylin (Muto Pure Chemicals, Japan) and eosin solution (Wako Pure Chemical Industries). NAFLD Activity score (NAS) was calculated according to the criteria of Kleiner (Kleiner D E. et al., *Hepatology*, 2005; 41:1313).

Statistical tests were performed using Bonferroni Multiple Comparison Test. P values <0.05 were considered statistically significant.

Results

Figure 11:
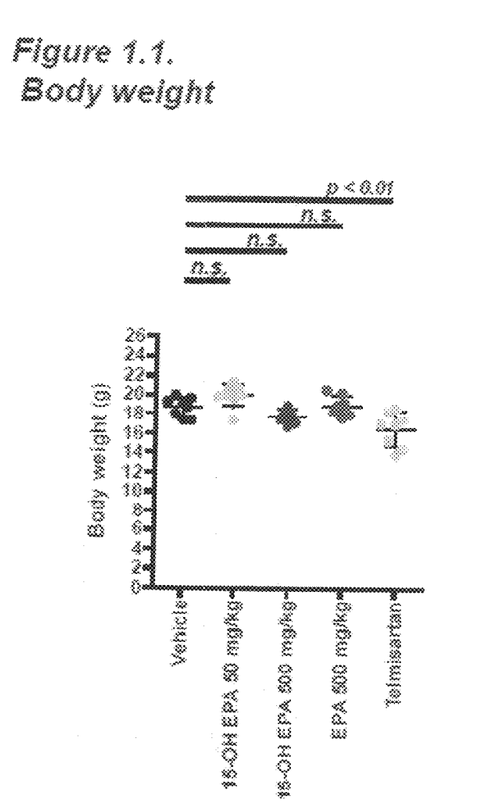

FIG. 1.1 shows that there was no significant change in body weight in any of the experimental groups.

Figure 12:
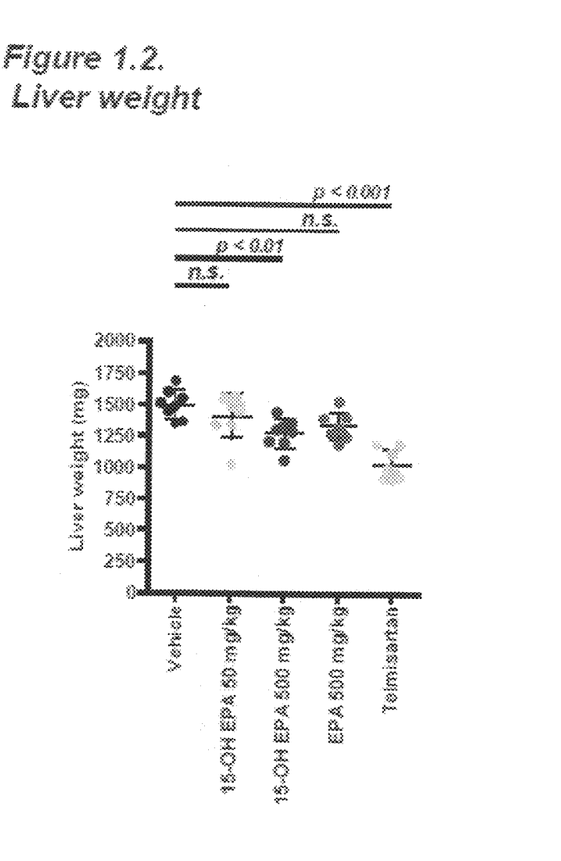

FIG. 1.2 shows that only the 15-OHEPA treatment group (500 mg/kg) and the positive control (telmisartan) had a significant reduction in liver weight as compared to the vehicle control.

Figures 2, 21:
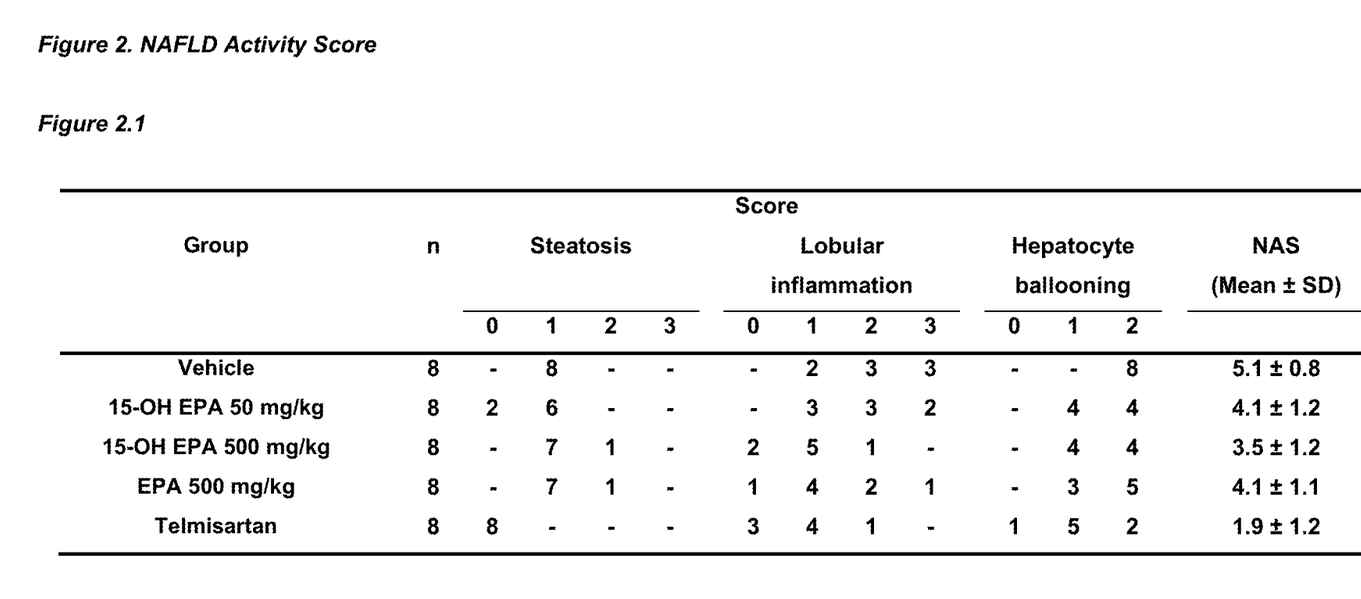
Figure 22:
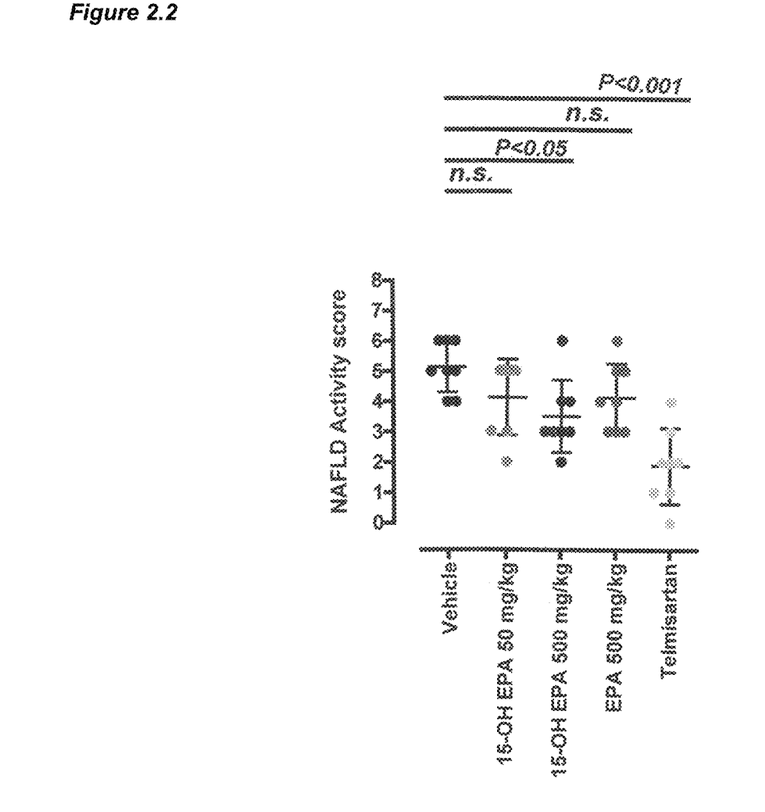

FIGS. 2.1 and 2.2 show that NAS significantly decreased only in the 15-OHEPA (500 mg/kg) and the positive control (telmisartan) groups as compared to the vehicle control.

We claim:

1. A method for treating or preventing non-alcoholic fatty liver disease (NAFLD) in a subject comprising, orally administering to the subject a pharmaceutical composition comprising 15-hydroxyeicosapentaenoic acid (15-HEPE) that represents at least about 60%, by weight, of all fatty acids present in the pharmaceutical composition, in an amount effective to treat or prevent NAFLD in the subject.

2. The method of claim 1, wherein the 15-HEPE is present in the pharmaceutical composition in an amount from about 1 mg to about 1000 mg.

3. The method of claim 1, wherein the 15-HEPE represents at least about 70%, by weight, of all fatty acids present in the pharmaceutical composition.

4. The method of claim 1, wherein the 15-HEPE represents at least about 90%, by weight, of all fatty acids present in the pharmaceutical composition.

5. The method of claim 1, wherein the 15-HEPE represents substantially all fatty acids present in the pharmaceutical composition.

6. The method of claim 1, wherein the 15-HEPE represents all fatty acids present in the pharmaceutical composition.

7. The method of claim 1, wherein the composition is free of any other omega-3 fatty acids.

8. The method of claim 1, wherein the administering step includes administering the pharmaceutical composition to the subject about 1 to about 4 times per day.

9. The method of claim 1, wherein the pharmaceutical composition is present in one or more dosage units.

10. The method of claim 9, wherein the one or more dosage units comprise orally deliverable capsules.

11. The method of claim 1, wherein the subject has a predisposition to develop and/or a diagnosis of NAFLD.

12. The method of claim 1, wherein the 15-HEPE represents at least about 95%, by weight, of all fatty acids present in the pharmaceutical composition.

13. A method for treating or preventing non-alcoholic steatohepatitis in a subject comprising, orally administering to the subject a pharmaceutical composition comprising 15-hydroxyeicosapentaenoic acid (15-HEPE) that represents at least 60%, by weight, of all fatty acids present in the pharmaceutical composition, in an amount effective to treat or prevent non-alcoholic steatohepatitis in the subject.

14. The method of claim 13, wherein the 15-HEPE is present in the pharmaceutical composition in an amount from about 1 mg to about 1000 mg.

15. The method of claim 13, wherein the 15-HEPE represents at least about 70%, by weight, of all fatty acids present in the pharmaceutical composition.

16. The method of claim 13, wherein the 15-HEPE represents at least about 90%, by weight, of all fatty acids present in the pharmaceutical composition.

17. The method of claim 13, wherein the 15-HEPE represents at least about 95%, by weight, of all fatty acids present in the pharmaceutical composition.

18. The method of claim 13, wherein the 15-HEPE represents substantially all fatty acids present in the pharmaceutical composition.

19. The method of claim 13, wherein the 15-HEPE represents all fatty acids present in the pharmaceutical composition.

20. The method of claim 13, wherein the composition is free of any other omega-3 fatty acids.

21. The method of claim 13, wherein the administering step includes administering the pharmaceutical composition to the subject about 1 to about 4 times per day.

22. The method of claim 13, wherein the pharmaceutical composition is present in one or more dosage units.

23. The method of claim 22, wherein the one or more dosage units comprise orally deliverable capsules.

24. The method of claim 13, wherein the subject has a predisposition to develop and/or a diagnosis of non-alcoholic steatohepatitis.

* * * * *